US009375325B2

(12) United States Patent
Garrec et al.

(10) Patent No.: US 9,375,325 B2
(45) Date of Patent: Jun. 28, 2016

(54) EXOSKELETON ARM HAVING AN ACTUATOR

(71) Applicant: COMMISSARIAT A L'ENERGIE ATOMIQUE ET AUX ENERGIES ALTERNATIVES, Paris (FR)

(72) Inventors: Philippe Garrec, Gif-sur-Yvette (FR); Yann Perrot, Sainte-Genevieve des Bois (FR); Dominique Ponsort, Bievres (FR); Aurelie Riglet, Dammaries sur Loing (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/395,865

(22) PCT Filed: May 28, 2013

(86) PCT No.: PCT/EP2013/060918
§ 371 (c)(1),
(2) Date: Oct. 21, 2014

(87) PCT Pub. No.: WO2013/182452
PCT Pub. Date: Dec. 12, 2013

(65) Prior Publication Data
US 2015/0119998 A1    Apr. 30, 2015

(30) Foreign Application Priority Data
Jun. 4, 2012   (FR) ...................................... 12 55177

(51) Int. Cl.
*A61F 2/54* (2006.01)
*A61F 2/00* (2006.01)
(Continued)

(52) U.S. Cl.
CPC .................. *A61F 2/54* (2013.01); *B25J 9/0006* (2013.01); *A61F 2/58* (2013.01); *A61F 2/581* (2013.01);
(Continued)

(58) Field of Classification Search
CPC ................................................ A61F 2002/5093
USPC ........................................................ 623/57–62
See application file for complete search history.

(56) References Cited

U.S. PATENT DOCUMENTS 2,535,489 A * 12/1950 Edwards .................... A61F 2/58
623/24
(Continued)

FOREIGN PATENT DOCUMENTS

FR    2 949 669 A1    3/2011

OTHER PUBLICATIONS

N. Jarrasse, et al., "Design and acceptability assessment of a new reversible orthosis", IEEE/RSJ International Conference on Intelligent Robots and Systems, Sep. 22-26, 2008, pp. 1933-1939.
(Continued)

*Primary Examiner* — Jacqueline Woznicki
(74) *Attorney, Agent, or Firm* — Sughrue Mion, PLLC

(57) ABSTRACT

The invention relates to an assist arm intended to be fitted on an exoskeleton, having a mounting plate (2) carrying a drive member (20), a shoulder segment (4) articulated on the mounting plate, an arm segment (6) having a proximal end articulated on the shoulder segment, a forearm segment (8) having a proximal end articulated on a distal end of the arm segment, an actuating cable (27) driven by the drive member and forming two strands (27a, 27b) which extend parallel to the first axis in order to pass through the first articulation and to wind around a receiving pulley (30) which is mounted in a rotating manner about the second axis and which rotates as one with the arm, and connecting means (31, 32, 33) coupled between the shoulder segment and the forearm second segment and arranged such that a flexion of the arm segment causes a concomitant flexion of the forearm segment.

10 Claims, 1 Drawing Sheet

(51) Int. Cl.
*A61F 2/58* (2006.01)
*A61F 2/68* (2006.01)
*B25J 9/00* (2006.01)
*A61F 2/50* (2006.01)
*A61F 2/78* (2006.01)

(52) U.S. Cl.
CPC .......... *A61F 2/582* (2013.01); *A61F 2/583* (2013.01); *A61F 2/585* (2013.01); *A61F 2/68* (2013.01); *A61F 2/78* (2013.01); *A61F 2002/5018* (2013.01); *A61F 2002/5038* (2013.01); *A61F 2002/5066* (2013.01); *A61F 2002/5081* (2013.01); *A61F 2002/5093* (2013.01); *A61F 2002/5096* (2013.01); *A61F 2002/543* (2013.01); *A61F 2002/546* (2013.01); *A61F 2002/7862* (2013.01)

(56) References Cited

U.S. PATENT DOCUMENTS

| | | | |
|---|---|---|---|
| 3,449,769 A * | 6/1969 | Mizen | A61F 2/54 601/23 |
| 4,180,870 A | 1/1980 | Radulovic et al. | |
| 4,373,517 A * | 2/1983 | Criscuolo | A61F 5/3753 602/20 |
| 4,669,451 A * | 6/1987 | Blauth | A61F 5/013 482/901 |
| 4,836,195 A * | 6/1989 | Berrehail | A61F 5/3753 602/19 |
| 4,862,878 A * | 9/1989 | Davison | A61F 5/0118 2/44 |
| 4,896,660 A * | 1/1990 | Scott | A61F 5/3753 602/20 |
| 5,033,461 A * | 7/1991 | Young | A61F 5/3753 602/16 |
| 5,167,612 A * | 12/1992 | Bonutti | A61F 5/0123 601/33 |
| 5,213,094 A * | 5/1993 | Bonutti | A61F 5/0123 601/33 |
| 5,282,460 A * | 2/1994 | Boldt | A61F 2/68 403/119 |
| 5,312,322 A * | 5/1994 | Santana | A61F 5/0118 602/20 |
| 5,383,844 A * | 1/1995 | Munoz | A61F 5/3738 602/20 |
| 5,385,536 A * | 1/1995 | Burkhead | A61F 5/3753 2/45 |
| 5,399,154 A * | 3/1995 | Kipnis | A61F 5/0125 602/16 |
| 5,437,619 A * | 8/1995 | Malewicz | A61F 5/0125 602/16 |
| 5,624,398 A * | 4/1997 | Smith | A61B 19/22 604/95.01 |
| 5,685,830 A * | 11/1997 | Bonutti | A61F 5/013 601/33 |
| 5,759,165 A * | 6/1998 | Malewicz | A61F 5/0125 602/16 |
| 5,800,561 A * | 9/1998 | Rodriguez | A61F 5/013 601/40 |
| 6,104,379 A * | 8/2000 | Petrich | G06F 3/011 345/156 |
| 6,113,562 A * | 9/2000 | Bonutti | A61F 5/013 602/16 |
| 6,821,259 B2 * | 11/2004 | Rahman | A61F 5/0102 601/24 |
| 7,252,644 B2 * | 8/2007 | Dewald | A61H 1/02 601/23 |
| 7,337,007 B2 * | 2/2008 | Nathan | A61N 1/0452 602/2 |
| 7,410,338 B2 * | 8/2008 | Schiele | A61H 1/0274 414/4 |
| 7,481,782 B2 * | 1/2009 | Scott | A61F 2/54 601/33 |
| 7,524,294 B1 * | 4/2009 | Shelton | A61H 1/0277 601/33 |
| 7,563,236 B2 * | 7/2009 | Kazmierczak | A61F 5/3753 602/4 |
| 7,670,306 B2 * | 3/2010 | Nordt, III | A41D 13/05 602/20 |
| 7,841,998 B2 * | 11/2010 | Pomeroy | A61B 17/6425 602/16 |
| 7,862,524 B2 * | 1/2011 | Carignan | A61H 1/0281 601/33 |
| 8,005,651 B2 * | 8/2011 | Summit | G06F 17/50 703/1 |
| 8,038,637 B2 * | 10/2011 | Bonutti | A61F 5/013 602/20 |
| 8,066,656 B2 * | 11/2011 | Bonutti | A61H 1/02 602/23 |
| 8,083,694 B2 * | 12/2011 | Peles | A61H 1/0277 601/33 |
| 8,251,934 B2 * | 8/2012 | Bonutti | A61F 5/055 602/18 |
| 8,273,043 B2 * | 9/2012 | Bonutti | A61F 5/013 602/23 |
| 8,277,396 B2 * | 10/2012 | Scott | A61B 5/1121 414/5 |
| 8,323,355 B2 * | 12/2012 | Latour | A61F 2/54 602/20 |
| 8,347,710 B2 * | 1/2013 | Scott | A61B 5/1038 414/2 |
| 8,366,647 B2 * | 2/2013 | Murinson | A61F 5/0118 128/846 |
| 8,409,118 B2 * | 4/2013 | Agrawal | A61H 1/0237 601/23 |
| 8,585,620 B2 * | 11/2013 | McBean | A61F 5/0127 600/546 |
| 8,613,716 B2 * | 12/2013 | Summit | A61F 5/013 602/19 |
| 8,622,939 B2 * | 1/2014 | Nguyen | A61H 1/0288 482/44 |
| 8,641,782 B2 * | 2/2014 | Kim | B25J 9/0006 414/5 |
| 8,795,207 B2 * | 8/2014 | Cavallaro | A61H 1/0274 601/23 |
| 8,801,639 B2 * | 8/2014 | Malosio | A61H 1/0274 482/139 |
| 8,821,588 B2 * | 9/2014 | Latour | A61F 2/54 602/16 |
| 8,834,169 B2 * | 9/2014 | Reinkensmeyer | A61H 1/0274 434/247 |
| 8,905,950 B2 * | 12/2014 | Bonutti | A61H 1/0237 128/845 |
| 8,926,534 B2 * | 1/2015 | McBean | A61F 5/0127 601/24 |
| 8,986,234 B2 * | 3/2015 | Summit | G06F 17/50 602/14 |
| 8,998,833 B1 * | 4/2015 | AlSaffar | A61F 5/013 602/20 |
| 9,017,271 B2 * | 4/2015 | Nef | A61H 1/0281 601/23 |
| 9,144,528 B2 * | 9/2015 | Agrawal | A61H 1/0274 |
| 2015/0018737 A1 * | 1/2015 | Threlfall | A61H 3/02 602/20 |
| 2015/0018739 A1 * | 1/2015 | Threlfall | A61H 3/02 602/23 |
| 2015/0119998 A1 * | 4/2015 | Garrec | B25J 9/0006 623/57 |

OTHER PUBLICATIONS

P. Garrec, et al., "ABLE, an Innovative Transparent Exoskeleton for the Upper-Limb", IEEE/RSJ International Conference on Intelligent Robots and Systems, Sep. 22-26, 2008, pp. 1483-1488.
Joel C. Perry, et al., "Upper-Limb Powered Exoskeleton Design", IEEE/ASME Transactions on Mechatronics, Aug. 1, 2007, vol. 12, No. 4.
International Search Report for PCT/EP2013/060918 dated Aug. 9, 2013 [PCT/ISA/210].

* cited by examiner

EXOSKELETON ARM HAVING AN ACTUATOR

The invention relates to an exoskeleton arm having a single actuator, which may advantageously be fixed to the dorsal part of an exoskeleton.

BACKGROUND OF THE INVENTION

There are various known assist arms which can be fitted to exoskeletons, and can be used in particular for lifting loads from below, for example a sack of sand or a patient. In general, these arms have shoulder, elbow and wrist articulations that are associated with respective motorizations, which makes the assembly heavy and complex. Furthermore, the motorizations are often in the form of transverse motors extending in continuation of the axis of the articulation, which entails significant encumbrance. In order to limit this encumbrance, it is therefore expedient to restrict the load which can be lifted, or to increase the down-gearing ratio between the motor and the driven segment, which tends to reduce the transparency of the articulation. This drawback may be partially overcome by torque feedback, but this requires the use of a torque sensor, making the solution less reliable, more complex and more expensive.

There are other solutions, for example lifting components which can be fitted to an exoskeleton and which comprise spring balancing instead of an actuator. Such a component needs to be adjusted beforehand for a given load, which greatly limits the range of its use.

OBJECT OF THE INVENTION

The object of the invention is to provide a simplified assist arm for an exoskeleton, the compactness of which makes it easy to integrate it with an ambulatory exoskeleton such as the HERCULE exoskeleton from the company Rb3d.

SUMMARY OF THE INVENTION

With a view to achieving this object, an assist arm intended to be fitted to an exoskeleton is provided, comprising:
  a mounting plate carrying a motor component;
  a shoulder segment articulated on the mounting plate by means of a first articulation about a first axis which is substantially vertical during use;
  an arm segment having a proximal end articulated on the shoulder segment by means of a second articulation about a second axis which is substantially perpendicular to the first axis;
  a forearm segment having a proximal end articulated on a distal end of the arm segment by means of a third articulation about a third axis which is substantially parallel to the second axis.

According to the invention, the assist arm furthermore comprises:
  at least one actuation cable driven by the motor component and forming two strands, which extend parallel to the first axis so as to pass through the first articulation and run around a receiving pulley which is mounted so as to rotate about the second axis and is linked in rotation with the arm;
  connecting means which are attached between the shoulder segment and the forearm segment and are arranged so that flexion of the arm segment leads to concomitant flexion of the forearm segment.

Thus, with the aid of a single motor component mounted on the mounting plate (and therefore positioned on the operator's back when the mounting plate is attached to the exoskeleton), it is possible to lift loads using the forearm. The assembly is very compact, and the motor component can be placed on the mounting plate, and therefore on the operator's back, so that it does not interfere with the operator's vision or the range of the movements of the assist arm.

The directions during use refer to articulation directions when the exoskeleton is being worn by an operator, the latter having an arm which cooperates with the assist arm in a resting position along the body.

According to a particular embodiment, the forearm comprises two subsegments articulated to one another by means of a fourth articulation about a fourth axis which is substantially perpendicular to the third axis. This arrangement allows free lateral movement of the end of the arm.

BRIEF DESCRIPTION OF THE DRAWINGS

The invention will be better understood from the following detailed description of a particular embodiment with reference to the figures of the appended drawings, in which.

DETAILED DESCRIPTION OF THE INVENTION

Figure 1:
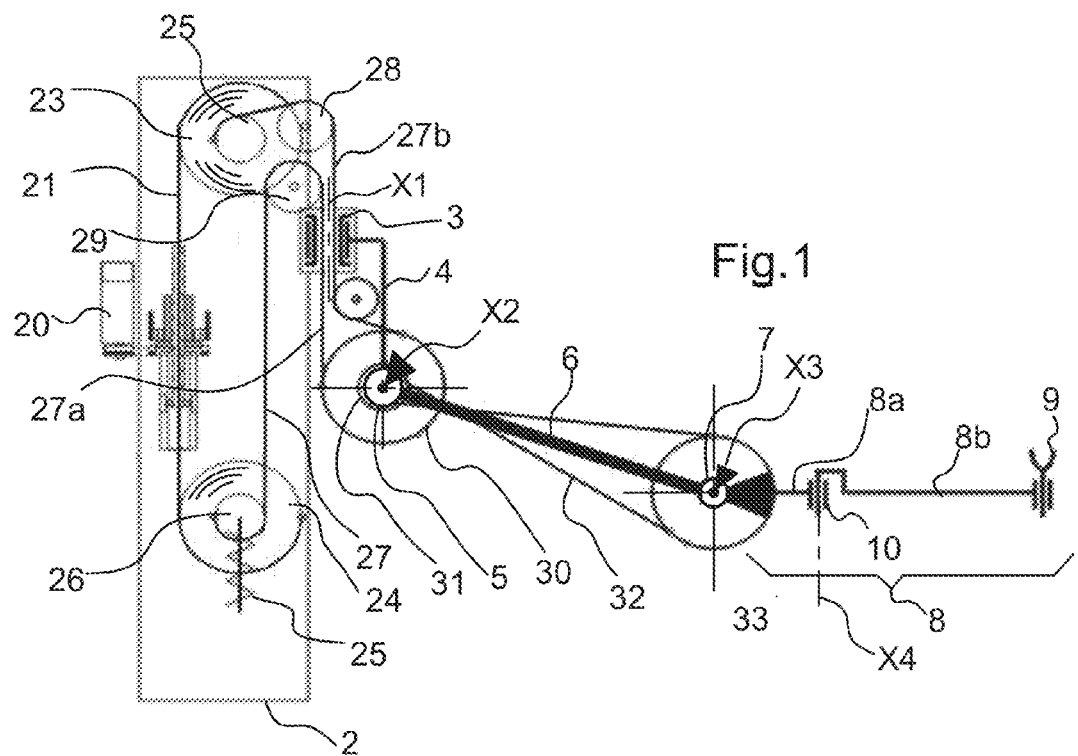
FIG. 1 is an outline diagram of the assist arm according to the invention.
Figure 2:
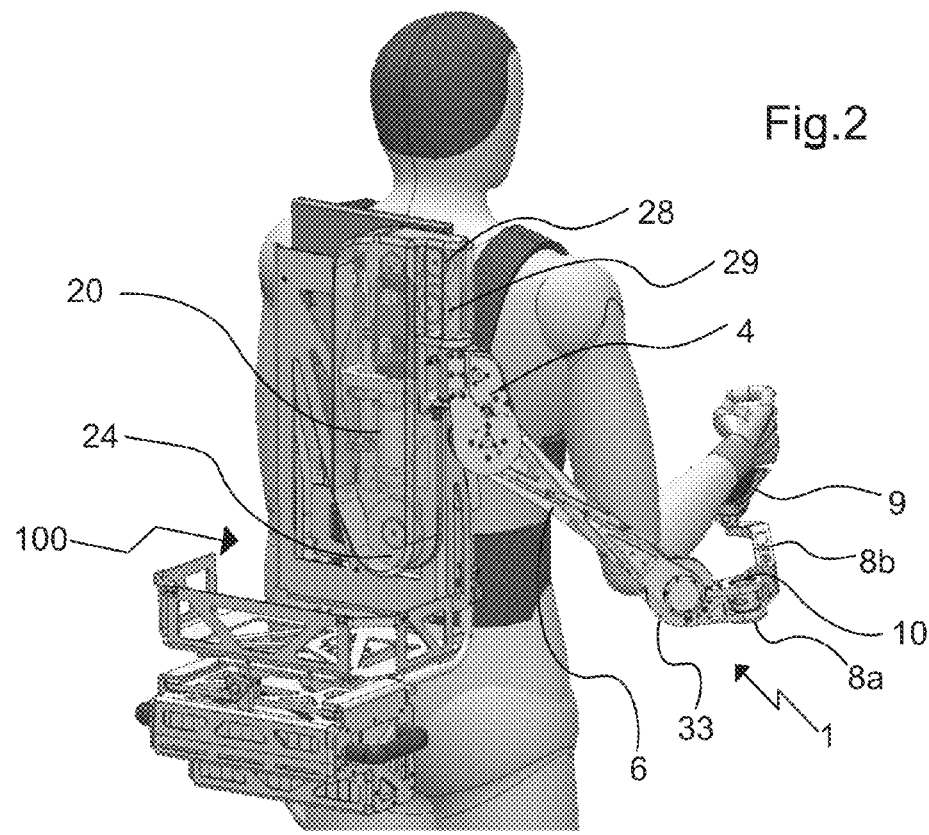
FIG. 2 is a view of an exoskeleton fitted with the assist arm of the invention and worn by a user.

With reference to the figures, the assist arm 1 of the invention comprises firstly a mounting plate 2, which carries a first articulation 3 making it possible to articulate a shoulder segment 4 about a first axis X1 which is vertical during use. The mounting plate 2 is advantageously equipped with means for attachment to the dorsal part of an exoskeleton 100, or at least a support structure worn by an operator.

The shoulder segment 4 carries a second articulation 5 making it possible to articulate the proximal end of an arm segment 6 about a second axis X2 (here seen end-on) which is substantially perpendicular to the first axis X1. The distal end of the arm segment 6 carries a third articulation 7, which makes it possible to articulate the proximal end of a forearm segment 8 about a third axis X3 (here seen end-on) substantially parallel to the second axis X2. The forearm segment 8 has a distal end which carries a handrest 9. Here, the forearm segment 8 is divided into two subsegments 8a, 8b, which are connected together by a fourth articulation 10 making it possible to articulate the two subsegments to one another about a fourth axis X4 which is substantially perpendicular to the third axis X3.

The assist arm 1 of the invention is provided with a motor component 20 carried by the mounting plate 2, here an electric motor, capable of driving a first cable 21 or drive cable by means of a cable actuator 22. The drive cable 21 comprises a strand tensioned between two first pulleys 23, 24 mounted so as to rotate on the mounting plate 2. The first pulley 24 is provided here with a tensioner 25 for maintaining a tension in the drive cable 21. The first pulleys 23, 24 are linked in rotation respectively with second pulleys 25, 26 having a diameter less than that of the first pulleys 23, 24. Attached to the second pulleys 25, 26, there is a second cable 27 or actuation cable, which, with the aid of two return pulleys 28, 29 mounted so as to rotate on the mounting plate 2, form two strands 27a, 27b which extend parallel to the first axis X1 while passing inside the first articulation 3, which is hollow. The two parallel strands 27a, 27b then separate and run around a receiving pulley 30 mounted so as to rotate about the second axis X2 while being linked in rotation with the arm segment 6.

Thus, when the electric motor 20 is operated, it causes movement of the drive cable 21 in one direction or the other, thereby causing movement of the actuation cable 27, which induces flexion of the arm segment 6. Passage of the strands 27a, 27b of the second cable through the first articulation (which is free) allows free rotation of the shoulder segment without causing flexion of the arm segment 6. The use of two cables wound around pulleys with different diameters allows step-down torque conversion.

The arm of the invention is furthermore equipped with connecting means making it possible to generate flexion of the forearm segment 8 in response to flexion of the arm segment 6. In the present case, these means comprise a coordination pulley 31 fixed to the shoulder segment 4 concentrically with the second axis X2. A third cable or coordination cable 32 is attached to the coordination pulley 31 and, after crossover of the strands, runs around a drive pulley 33 mounted so as to rotate about the third axis X3 while being linked in rotation with the forearm segment 8. By virtue of these connecting means, flexion of the arm segment 6, caused by the motor 20, induces concomitant flexion of the forearm segment 8 in the same direction. By varying the respective diameters of the coordination pulley and of the drive pulley, the amplitude of the flexion of the forearm segment as a function of the amplitude of the flexion of the arm segment is adjusted accurately.

Such an assist arm has several advantages. Firstly, it uses only a single motor component, located on the operator's back. It also makes it possible to lift a load from below. Furthermore, actuation by a cable actuator makes it possible to position a long motor mounted flat on the mounting plate (and therefore on the user's back), leading to a very thin assist arm with very transparent transmission (low inertia and friction), making it possible to obviate feedback by a torque sensor. Lastly, the arm is self-contained and can be removed easily from the exoskeleton.

The invention is not limited to that which has been described above, but rather covers any variant falling within the scope defined by the claims.

In particular, although the connecting component between the shoulder segment and the forearm segment comprises two pulleys and an associated coordination cable in this case, other connecting components may be used, such as a link rod attached between the shoulder segment and the forearm segment.

Although the actuation in this case employs a double-loop cable actuator with two cables, making it possible to increase the force of the cylinder with a negligible loss of energy, single-cable actuation may be used. In this case, the cable actuator will act directly on the actuation cable.

The invention claimed is:

1. An assist arm intended to be fitted to an exoskeleton, comprising:
   a mounting plate carrying a motor component;
   a shoulder segment articulated on the mounting plate by means of a first articulation about a first axis which is vertical during use;
   an arm segment having a proximal end articulated on the shoulder segment by means of a second articulation about a second axis which is perpendicular to the first axis;
   a forearm segment having a proximal end articulated on a distal end of the arm segment by means of a third articulation about a third axis which is parallel to the second axis;
   at least one actuation cable driven by the motor component and forming two strands, which extend parallel to the first axis so as to pass through the first articulation and be wound around a receiving pulley which is mounted so as to rotate about the second axis and is linked in rotation with the arm; and
   connecting means which are attached between the shoulder segment and the forearm segment and are arranged so that flexion of the arm segment leads to concomitant flexion of the forearm segment.

2. The assist arm as claimed in claim 1, wherein the motor component is associated with a cable actuator which drives a drive cable tensioned between two first pulleys mounted so as to rotate on the mounting plate, the actuation cable attached to two second pulleys respectively linked to the first pulleys and having a diameter less than a diameter of the first pulleys.

3. The assist arm as claimed in claim 1, wherein the forearm segment comprises a distal end provided with a handrest.

4. The assist arm as claimed in claim 1, wherein the connecting means between the shoulder segment and the forearm segment comprise a coordination pulley concentric with the second axis but fixed on the shoulder segment, a drive pulley mounted so as to rotate about the third axis while being linked to the forearm segment, and a coordination cable wound with strand crossover on the coordination pulley and the drive pulley.

5. The assist arm as claimed in claim 1, wherein the forearm segment comprises two subsegments articulated to one another by means of a fourth articulation about a fourth axis which is perpendicular to the third axis.

6. An assist arm intended to be fitted to an exoskeleton, comprising:
   a mounting plate carrying a motor component;
   a shoulder segment articulated on the mounting plate about a first axis extending upwards during use;
   an arm segment having a proximal end articulated on the shoulder segment about a second axis which extends transverse to the first axis;
   a forearm segment having a proximal end articulated on a distal end of the arm segment about a third axis which extends transverse to the first axis;
   at least one actuation cable driven by the motor component and forming two strands, which pass in part along the first axis and wind around a receiving pulley which is mounted so as to rotate about the second axis and is linked in rotation with the arm; and
   a connecting assembly comprising a coordination pulley and a drive pulley and a coordination cable attached between the shoulder segment and the forearm segment and arranged so that flexion of the arm segment leads to concomitant flexion of the forearm segment.

7. The assist arm as claimed in claim 6, wherein the motor component is associated with a cable actuator that drives a drive cable tensioned between two first pulleys mounted so as to rotate on the mounting plate, the actuation cable attached to two second pulleys respectively linked to the first pulleys and having a diameter less than a diameter of the first pulleys.

8. The assist arm as claimed in claim 6, wherein the forearm segment comprises a distal end provided with a handrest.

9. The assist arm as claimed in claim 6, wherein one of the coordination pulley and drive pulley is concentric with the second axis and fixed on the shoulder segment, and the other of the coordination pulley and the drive pulley is mounted so as to rotate about the third axis while being linked to the forearm segment, and the coordination cable is wound around the coordination pulley and the drive pulley.

10. The assist arm as claimed in claim 6, wherein the forearm segment comprises two subsegments articulated to one another about a fourth axis which extends upwards during use.

* * * * *